US00PP19730P2

(12) United States Plant Patent
Arts

(10) Patent No.: US PP19,730 P2
(45) Date of Patent: Feb. 17, 2009

(54) ***HYDRANGEA* PLANT NAMED 'AGRIHYDRAEEN'**

(50) Latin Name: *Hydrangea hybrida*
Varietal Denomination: Agrihydraeen

(75) Inventor: Niels Arts, Aalsmeer (NL)

(73) Assignee: Agriom B.V., De Kwakel (NL)

( * ) Notice: Subject to any disclaimer, the term of this patent is extended or adjusted under 35 U.S.C. 154(b) by 0 days.

(21) Appl. No.: 12/074,413

(22) Filed: Mar. 3, 2008

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent L Bell
(74) *Attorney, Agent, or Firm*—C. A. Whealy

(57) ABSTRACT

A new and distinct cultivar of *Hydrangea* plant named 'Agrihydraeen', characterized by its upright and mounded plant habit; strong roots and stems; freely branching habit; and large inflorescences with purple-colored flowers with light pink-colored margins.

1 Drawing Sheet

Botanical designation: *Hydrangea hybrida.*
Cultivar denomination: 'Agrihydraeen'.

BACKGROUND OF THE INVENTION

The present invention relates to a new and distinct cultivar of *Hydrangea,* botanically known as *Hydrangea hybrida* and hereinafter referred to by the name 'Agrihydraeen'.

The new *Hydrangea* is a product of a planned breeding program conducted by the Inventor in Aalsmeer, The Netherlands. The objective of the breeding program was to create new *Hydrangea* cultivars with strong stems, large inflorescences and attractive flower color.

The new *Hydrangea* originated from a cross-pollination made by the Inventor on Apr. 15, 2001 in Aalsmeer, The Netherlands, of a proprietary selection of *Hydrangea hybrida* identified as code number 200005, not patented, as the female, or seed, parent with a proprietary selection of *Hydrangea hybrida* identified as code number 200108-06, not patented, as the male, or pollen, parent. The new *Hydrangea* was discovered and selected by the Inventor as a single flowering plant within the progeny of the stated cross-pollination in a controlled environment in Glandorf, Germany on Mar. 15, 2003.

Asexual reproduction of the new *Hydrangea* by vegetative cuttings in a controlled environment in a greenhouse in Aalsmeer, The Netherlands since Mar. 15, 2004, has shown that the unique features of this new *Hydrangea* are stable and reproduced true to type in successive generations.

SUMMARY OF THE INVENTION

The cultivar Agrihydraeen has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Agrihydraeen'. These characteristics in combination distinguish 'Agrihydraeen' as a new and distinct cultivar of *Hydrangea:*

1. Upright and mounded plant habit.
2. Strong roots and stems.

3. Freely branching habit.
4. Large inflorescences with purple-colored flowers with light pink-colored margins.

Plants of the new *Hydrangea* differ from plants of female parent selection primarily in branching habit as plants of the new *Hydrangea* are more freely branching than plants of the female parent selection.

Plants of the new *Hydrangea* differ from plants of male parent selection primarily in flower color as plants of the male parent selection have reddish pink-colored flowers.

Plants of the new *Hydrangea* can be compared to plants of the cultivar Doris, not patented. Plants of the new *Hydrangea* differ from plants of the cultivar Doris in the following characteristics:

1. Plants of the new *Hydrangea* are more vigorous than plants of the cultivar Doris.
2. Plants of the new *Hydrangea* have stronger stems than plants of the cultivar Doris.
3. Plants of the new *Hydrangea* have larger leaves than plants of the cultivar Doris.
4. Plants of the new *Hydrangea* are more freely flowering than plants of the cultivar Doris.
5. Plants of the new *Hydrangea* and the cultivar Doris differ in flower color as plants of the cultivar Doris have purple-colored flowers.

BRIEF DESCRIPTION OF THE PHOTOGRAPH

The accompanying colored photograph illustrates the unique appearance of the new cultivar, showing the colors as true as it is reasonably possible to obtain in colored reproductions of this type. Colors in the photograph may differ from the color value cited in the detailed botanical description which accurately describe the colors of the new *Hydrangea.* The photograph comprises a side perspective view of a typical flowering plant of 'Agrihydraeen' grown in a container.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photograph and in the following description were grown during the winter in De Kwakel, The Netherlands, in 15-cm containers in a glass-covered greenhouse and under conditions which closely approximate commercial production conditions. During the production of the plants, day and night temperatures averaged 17° C. Plants of the new *Hydrangea* were about one year old when the photograph and description were taken.

Botanical description: *Hydrangea hybrida* cultivar Agrihydraeen.

Parentage:

*Female, or seed, parent.*—Proprietary selection of *Hydrangea hybrida* identified as code number 20005, not patented.

*Male, or pollen, parent.*—Proprietary selection of *Hydrangea hybrida* identified as code number 200108-06, not patented.

Propagation:

*Type cutting.*—By vegetative cuttings.

*Time to initiate roots, summer.*—About 14 days at temperatures of 23° C.

*Time to initiate roots, winter.*—About 18 days at temperatures of 18° C.

*Time to produce a rooted young plant, summer.*—About four weeks at temperatures of 23° C.

*Time to produce a rooted young plant, winter.*—About five weeks at temperatures of 18° C.

*Root description.*—Thick; whitish brown in color.

*Rooting habit.*—Freely branching; dense.

Plant description:

*Form/growth habit.*—Upright and mounded plant habit; inverted triangle. Strong lateral branches; vigorous growth habit.

*Plant height.*—About 30 cm to 40 cm.

*Plant diameter or area of spread.*—About 40 cm.

*Branching habit.*—When pinched, freely branching with about six lateral branches per plant.

*Lateral branches.*—Length: About 25 cm. Diameter: About 4 mm. Internode length: About 7 cm. Texture: Smooth, glabrous. Strength: Strong. Color: Close to 146C.

Foliage description:

*Arrangement.*—Opposite, simple.

*Length.*—About 13 cm.

*Width.*—About 7.5 cm.

*Shape.*—Ovate.

*Apex.*—Acute to acuminate.

*Base.*—Obtuse.

*Margin.*—Dentate to serrate.

*Texture, upper and lower surfaces.*—Rugose; glabrous.

*Venation pattern.*—Pinnate.

*Color.*—Developing foliage, upper surface: Close to 137A. Developing foliage, lower surface: Close to 137D. Fully expanded foliage, upper surface: Close to 137A; venation, 146B. Fully expanded foliage, lower surface: Close to 147B; venation, 146D.

*Petiole.*—Length: About 1.5 cm. Diameter: About 2 mm. Texture, upper and lower surfaces: Smooth, glabrous. Color, upper surface: Close to 146B. Color, lower surface: Close to 146D.

Flower description:

*Flower type and habit.*—Single sterile and fertile flowers arranged on terminal panicles; panicles large and globular. Flowers face upright to outward. Flowers persistent. Flowers not fragrant.

*Natural flowering season.*—Continuous flowering during the summer in Northern Europe.

*Flower longevity.*—Sterile flowers last about four months on the plant; fertile flowers last about one month on the plant.

*Quantity of flowers.*—Freely flowering; about 70 sterile flowers per panicle and about 50 fertile flowers per panicle.

*Panicle height.*—About 11 cm.

*Panicle diameter.*—About 15 cm.

*Sterile flower diameter.*—About 4.5 cm.

*Sterile flower depth (height).*—About 1.5 cm.

*Fertile flower diameter.*—About 6 mm.

*Fertile flower depth (height).*—About 7 mm.

*Flower buds.*—Length: About 3 mm. Diameter: About 3 mm. Shape: Flattened globular. Color: Close to 144A.

*Petals, sterile flowers only, fertile flowers without petals.*—Arrangement: About four in a single whorl. Length: About 3.5 mm. Width: About 2.5 mm. Shape: Ovate. Apex: Acute. Base: Attenuate. Margin: Entire. Texture, upper and lower surfaces: Smooth, glabrous. Color: When opening, upper surface: Close to 78D. When opening, lower surface: Close to 78C. Fully opened, upper surface: Close to 78B; color becoming closer to 78C with development. Fully opened, lower surface: Close to 78C.

*Sepals, sterile flowers.*—Quantity per flower: About four in a single whorl. Length: About 2.5 cm. Width: About 2.5 cm. Shape: Deltoid. Apex: Acute to obtuse. Base: Cuneate. Margin: Entire. Texture, upper surface: Smooth, glabrous. Texture, lower surface: Rugose, glabrous. Color, upper surface: Close to 78C, towards the margin, 69D. Color, lower surface: Close to 186C.

*Sepals, fertile flowers.*—Quantity per flower: About four in a single whorl. Length: About 3.5 mm. Width: About 2 mm. Shape: Ovate. Apex: Acute. Base: Obtuse. Margin: Entire. Texture, upper and lower surfaces: Smooth, glabrous. Color, upper and lower surfaces: Close to 78D.

*Pedicels, sterile flowers.*—Angle: About 45° from vertical. Strength: Strong. Length: About 2.5 cm. Diameter: About 2 mm. Texture: Smooth, glabrous. Color: Close to 73A.

*Pedicels, fertile flowers.*—Angle: Mostly upright. Strength: Moderately strong. Length: About 2 mm. Diameter: About 1 mm. Texture: Smooth, glabrous. Color: Close to 66D.

*Reproductive organs, fertile flowers only; sterile flowers without reproductive organs.*—Stamens: Quantity per flower: About eight. Anther shape: Conical. Anther length: About 1 mm. Anther color: Close to 145D. Pollen amount: Abundant. Pollen color: Close to 155D. Pistils: Pistil quantity per flower: About three. Pistil length: About 1 mm. Stigma shape: Oval. Stigma color: Close to 155D. Style length: About 1 mm. Style color: Close to 155B. Ovary color: Close to 145C.

*Seeds.*—Length: About 0.5 mm. Diameter: About 0.1 mm. Color: Close to 200C.

Disease/pest resistance: Under commercial production conditions, plants of the new *Hydrangea* have not been observed to be resistant to pathogens or pests common to *Hydrangea.*

Temperature tolerance: Plants of the new *Hydrangea* have been shown to be tolerant to temperatures ranging from about 3° C. to about 38° C.

It is claimed:

1. A new and distinct *Hydrangea* plant named 'Agrihydraeen' as illustrated and described.

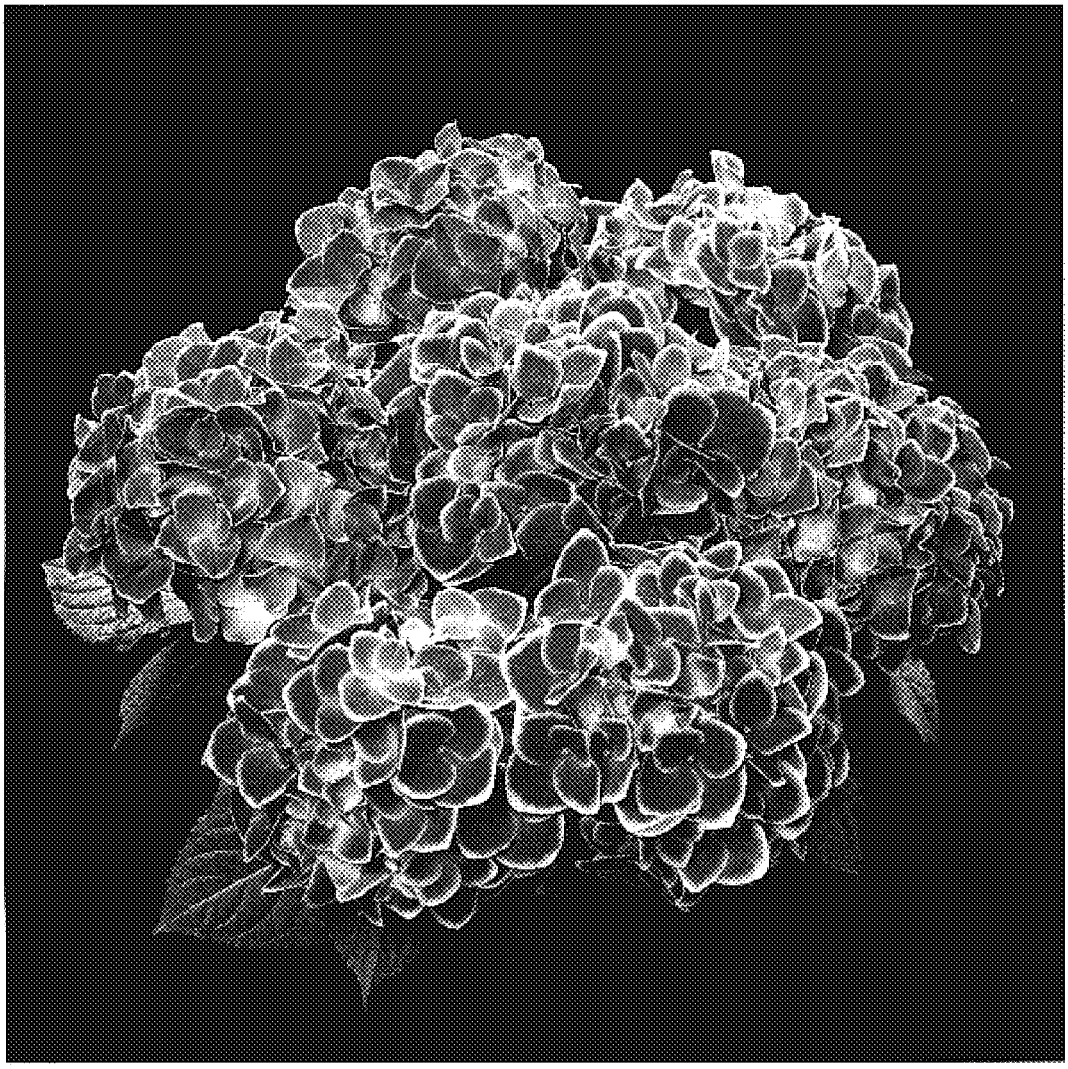

* * * * *